(12) United States Patent
Warren et al.

(10) Patent No.: US 9,706,951 B2
(45) Date of Patent: *Jul. 18, 2017

(54) METHODS FOR ASSESSING VAGINAL ATROPHY (71) Applicant: The Procter & Gamble Company, Cincinnati, OH (US)

(72) Inventors: Raphael Warren, Amberley Village, OH (US); Dean Larry DuVal, Lebanon, OH (US); Miranda Aref Farage, Mason, OH (US); Charles Carson Bascom, Liberty Township, OH (US); Gina Marie Fadayel, Maineville, OH (US); Kenneth Robert Wehmeyer, Cincinnati, OH (US); Jay Patrick Tiesman, Hamilton, OH (US); David Burton Moore, Hamilton, OH (US); Murray A. Friedman, Augusta, GA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/005,594

(22) Filed: Jan. 25, 2016

(65) Prior Publication Data

US 2016/0135722 A1  May 19, 2016

Related U.S. Application Data

(63) Continuation of application No. PCT/US2015/039860, filed on Jul. 10, 2015.

(60) Provisional application No. 62/023,479, filed on Jul. 11, 2014.

(51) Int. Cl.
  A61B 5/1477 (2006.01)
  A61B 5/145 (2006.01)
  G01N 33/68 (2006.01)
  A61B 5/00 (2006.01)
  G01N 33/50 (2006.01)

(52) U.S. Cl.
  CPC ........ *A61B 5/14539* (2013.01); *A61B 5/1477* (2013.01); *A61B 5/14546* (2013.01); *A61B 5/4337* (2013.01); *A61B 5/4848* (2013.01); *G01N 33/5091* (2013.01); *G01N 33/689* (2013.01); *G01N 33/6893* (2013.01); *G01N 2800/362* (2013.01); *G01N 2800/7095* (2013.01)

(58) Field of Classification Search
  None
  See application file for complete search history.

(56) References Cited

FOREIGN PATENT DOCUMENTS

RU   2404430   11/2010

OTHER PUBLICATIONS

Hummelen et al., *Vaginal Microbiome and Epithelial Gene Array in Post-Menopausal Women with Moderate to Severe Dryness*, PLoS ONE, Nov. 2011, vol. 6, Issue 11, pp. 1-8.
MacBride et al., *Vulvovaginal Atrophy*, Mayo Clinic Proceedings, Dowden Health Media Inc. US. vol. 85, No. Jan. 1, 2010.
(Continued)

*Primary Examiner* — Karen S Weiler
(74) *Attorney, Agent, or Firm* — Andres E. Velarde (57) ABSTRACT

An array of methods for assessing vaginal atrophy are disclosed. The methods may be used alone or in combination with a treatment or as part of a kit.

12 Claims, 2 Drawing Sheets
(1 of 2 Drawing Sheet(s) Filed in Color)

METHODS FOR ASSESSING VAGINAL ATROPHY (56) References Cited

OTHER PUBLICATIONS

Farage et al., *Urogenial Biomolecular and Physical Measures in Pre- and Post-Menopausal Women*, Journal of Clinical Gynecology and Obstetrics, vol. 4, No. 3, Jan. 1, 2015.
Farage et al., *Jacobs Journal of Experimental Dermatology and Research Possible Correlation Between Self-Reported Sensitive Skin and Physical and Chemical Biomarkers*, JJ Expt. Derm Res., Apr. 21, 2015, pp. 1-4.
PCT International Search Report, mailed Oct. 19, 2015, 15 pages.

METHODS FOR ASSESSING VAGINAL ATROPHY

METHODS FOR ASSESSING VAGINAL ATROPHY

FIELD OF THE INVENTION

The present invention relates to methods for assessing for vaginal atrophy involving sensorial sensors, pH, biochemistry, genomics, and/or histology of the labia and the introitus.

BACKGROUND OF THE INVENTION

Menopause is a normal natural aging event that affects all women. Menopause can be defined as the cessation of ovulation and menses for at least 12 months with no obvious pathological cause. The typical age for menopause is 51 years and it is estimated that in the US today (2010 Census) there are more than 53 million women who are of postmenopausal age (50+ years). Additional women fall into the post-menopausal category by virtue of a total hysterectomy (removal of uterus and both ovaries). Associated with post-menopause is a dramatic decline in circulating estradiol to less than 10% of the level that is typical during a woman's reproductive years. The reduced estrogen sets in motion major anatomic changes leading to unique symptoms and quality of life issues.

While decreasing estrogen has been reported to have a systemic effect on a woman's body, skin, and hair, the effect is also seen on the urogenital area, being diagnosed as vaginal atrophy or VA. VA assessment may require the insertion of a speculum into the woman's vagina. Subjective assessments are made that include loss of hymenal ruggae, presence of patulousness of the urethra, a telescoping vestibule, presence of petechiae in the vagina, and loss of elasticity that is digitally (finger) diagnosed at the introitus. The predominant symptoms reported by women include a feeling of vaginal dryness, pain with sexual penetration, bleeding with sexual penetration, vaginal itch, and genital skin itch; among others.

Objective measures and testing methods for VA rely on testing in the vagina at the mucosal surface. The hymen is a membrane that surrounds or partially covers the external vaginal opening (the tissue surrounding this opening can be referred to as the hymenal ring). The hymen is the limit between the internal and external genitalia. It consists of a thin fibrous membrane lining the lower vagina, covered on its external surface by a keratinized stratified squamous epithelium and on the internal surface by nonkeratinizing stratified squamous epithelium with glycogen (like the vaginal epithelium). For many women with VA, the hymen may constrict and lose elasticity thereby making it difficult or unpleasant to objectively be tested for VA. The tissue associated with the vaginal opening is also referred to as the introitus. Objective measures of VA are largely restricted to vaginal pH (typically requiring a speculum to create adequate access) where a pH of greater than or equal to 5.5 has been classified as a sign of VA. Vaginal scraping of the epithelial lining (also requiring a speculum insertion into the vagina) can be analyzed for the relative abundance of mature cells (called vaginal maturation index or VMI). However, the relationship between the VMI to VA varies among clinicians, and the variation can be quite broad. Similarly there is no clear relationship between a woman's symptomology and clinical assessment, or objective measures of vaginal pH.

Another potential objective method for diagnosing VA and the effect of a treatment might include the collection of a vaginal biopsy for transcriptional profiling. Obtaining a vaginal biopsy is quite difficult, requiring the use of a speculum. Further, one cannot be precise as to where the biopsy is derived nor ensure uniform properties of the biopsy. For example, differences in biopsy thickness can bias data derived from the dermis.

Further, with the exception of vaginal pH, all the other methods are subjective and not reliable. Another problem is that all the vaginal procedures such as the subjective vaginal atrophy grading or collecting vaginal pH or collecting vaginal scrapings for the VMI require the insertion of a speculum into the vagina. This procedure can be quite painful especially among women who suffer from VA. While the speculum can be lubricated (typically with commercial ultrasound gel) for easier insertion, this can compromise the collection of pH and VMI. The pain caused by the insertion of a speculum may influence whether a woman decides to seek diagnosis and treatment for VA.

As such there is a need for VA diagnostic methods and methods to assess the potential efficacy of treatments for VA that do not rely on the use of a speculum, sampling of vaginal tissue, and reduce the level of subjectivity by using a quantitative and objective method.

SUMMARY OF THE INVENTION

An array of one or more methods for identifying urogenital changes associated with vaginal atrophy is disclosed. The array of methods include: measuring pH at the labia majora, labia minora, introitus, or combinations thereof; determining brush sensitivity at the introitus; assessing glycogen amount at the introitus; taking a biopsy at the introitus and analyzing epithelial cells at the introitus; assessing protein amount testing at the introitus or the labia majora or the labia minora; assessing metabolites amounts at the introitus or the labia majora or the labia minora; assessing histamine amount at the introitus or the labia majora or the labia minora; transcriptomic heat mapping at the labia majora or the labia minora or the introitus; and evaluating gene expression at the labia majora for a set gene probe set.

A method of assessing efficacy of a vaginal atrophy treatment regimen is further disclosed. The method of assessing efficacy of a vaginal atrophy treatment regime includes: pretreatment assessment of vaginal atrophy using one or more diagnostic methods; applying one or more topical treatments to the labia majora, labia minora, introitus, vagina, or combinations thereof; post-treatment assessment of the vaginal atrophy state using the same diagnostic methods as used in the pretreatment assessment of vaginal atrophy; and determining the difference between the pretreatment and post-treatment assessments of vaginal atrophy to assess the overall effect of the topical treatment. The one or more diagnostic methods used in the pretreatment and post-treatment include: measuring pH at the labia majora, labia minora, introitus, or combinations thereof; determining brush sensitivity at the introitus; assessing glycogen testing at the introitus; biopsy analysis of the epithelial cells at the introitus; assessing protein testing at the introitus; transcriptomics heat mapping at the labia majora or the labia minora; evaluating gene expression at the labia majora for a set gene probe; post-treatment assessment of the vaginal atrophy state using the same diagnostic methods as used in the pretreatment assessment of vaginal atrophy; and determining the difference between the pretreatment and post-treatment assessments of vaginal atrophy to assess the overall effect of the topical treatment.

A kit for assessing efficacy of a vaginal atrophy treatment regimen comprising; a pretreatment assessment method for vaginal atrophy comprising; a topical treatment for application to the labia majora, labia minora, introitus, vagina, or combinations thereof; a post-treatment assessment method for vaginal atrophy state comprising the same diagnostic methods as used in the pretreatment assessment of vaginal atrophy; and a means to determine the difference between the pretreatment and post-treatment assessments of vaginal atrophy to assess the overall effect of the topical treatment. The one or more diagnostic methods used in the pretreatment and post-treatment include: measuring pH at the labia majora, labia minora, introitus, or combinations thereof; determining brush sensitivity at the introitus; assessing Glycogen testing at the introitus; biopsy analysis of the epithelial cells at the introitus; assessing protein testing at the introitus; transcriptnomics heat mapping at the labia majora or the labia minora; or evaluating gene expression at the labia majora for a set gene probe.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

The methods included in the array of methods of the present invention for assessing vaginal atrophy and assessing the efficacy of treatments for vaginal atrophy do not require the use of a speculum nor access to the vagina. The following array of methods reduces the level of subjectivity by using a quantitative and objective method. It is understood that one may rely on a single method or a combination of the methods described below. The following methods utilize sites other than the vaginal canal which are easily accessible and that can be used to objectively measure changes associated with urogenital atrophy and that don't require invasive tools such as a speculum. Furthermore these sites may be closely associated with the symptoms women report and the efficacy of treatments. These sites include the labia and the hymenal ring of the urogenital area. Both sites are particularly attractive due to their accessibility. The hymenal ring, like the vagina, is a mucosal surface, unlike the stratified epithelia of the labia.

The following methods, utilizing the labia and the hymenal ring (or introitus), may include pH, histology, sensitivity to a brush wiping, profiling of metabolites, and profiling of gene transcripts. Metabolites were identified analytical tools such as GC-MS and quantified from extracts derived from brush samples and tape strips.

Measuring pH at the Labia Majora, Labia Minora, and Hymenal Ring

Someone who is skilled in the art may not be restricted by this description.

pH may be measured using commercially available pH paper or a flathead pH probe. Non-limiting examples of pH paper or pH strips include pHydrion papers (3.0-5.5 range; Hydrion MicroEssentials Laboratory Inc., New York, N.Y., USA) and pHion Diagnostic Test Strips (4.5-9.0 range; iHerb.com). A non-limiting example of a flathead pH probe includes, for example, the SkinCheck HI-98109 (Hanna Instruments, Woonsocket, R.I., USA).

The pH may be measured using a pH strip by holding the pH strip using forceps to place the pH strip in contact with the desired area for 30 seconds.

The procedure for using the pH probe is as follows.

1. Prior to using the pH probe, remove the protective cap and condition the electrode by soaking the tip (preferably within 5 cm/2 inches off the bottom edge, more preferably within 3 cm/1.5 inches off the bottom edge) in fresh pH 7 buffer solution (for example solution HI7007P from Hanna Instruments) for 1 hour to as long as 24 hours. During the conditioning, the probe should be in the 'Off' position.

2. Calibrate the pH Probe. Turn the pH probe on. First, rinse the conditioned probe in distilled water, preferably deionized distilled water. Dip the probe electrode tip in pH 7 buffer (buffer that is less than 30 days old, preferably fresh buffer). Allow the reading to stabilize (i.e., preferably less than 1 hr., more preferably less than 15 minutes). After the reading stabilizes, use a small screwdriver to adjust to pH 7.00+/−0.02 with the trimmer (top left screw as you look at display of electrode) to read 7.00. Rinse the electrode tip with water (i.e., distilled water, preferably deionized distilled water), shake off excess, and repeat process using fresh pH 4.0 buffer (for example solution HI70004P from Hanna Instruments). Allow the reading to stabilize (i.e., preferably less than 1 hr., more preferably less than 15 minutes). After the reading stabilizes, use a small screwdriver to adjust to pH 4.00+/−0.02 with the trimmer (top right as you look at display of electrode) to read 4.00. The meter is ready for taking measurements. The probe tip can be left in either buffer solution (preferably within 5 cm/2 inches off the bottom edge, more preferably within 3 cm/1.5 inches off the bottom edge) for up to 2 hours.

3. Measurements. The pH meter switch should be ON. Rinse the electrode tip with distilled water, preferably deionized distilled water, and allow the excess water to drip off or gently shake off excess. Hold the electrode tip 45-135 degrees off the skin surface, preferably 60-120 degrees off the skin surface, and more preferably 75-105 degrees off the skin surface. Allow the pH probe display to stabilize for less than 15 minutes, preferably less than 5 minutes, more preferably less than 1 minute. After use, rinse the electrode tip with water (i.e., distilled water, preferably deionized distilled water), shake off excess, and begin to take a measurement at another urogenital site of the same subject. If the probe is not being used immediately, the probe can be rinsed with water (i.e., distilled water, preferably deionized distilled water) and transferred into a bath of either pH 4.0 or 7.0 buffer until use for up to 2 hours.

4. After Use or between Subjects. After the pH meter has been used turn the meter switch to the OFF position. To either store the pH probe or use on another subject, one needs to decontaminate or disinfect the pH probe. This is accomplished in one of two preferable ways. One way is by immersing the probe (preferably within 5 cm/2 inches off the bottom edge, more preferably within 3 cm/1.5 inches off the bottom edge) in 70% isopropyl alcohol preferably for 20 to 40 minutes, more preferably for 25 to 35 minutes. The probe is then rinsed with water (i.e., distilled water, preferably deionized distilled water) and recalibrated. Alternatively, one can use a germicidal hand wipe (Sani-Cloth HB alcohol free from PDI, Orangeburg, N.Y., USA) or spray (Citrex Hospital Spray Disinfectant from Cardinal Health, Columbus, Ohio, USA). After application, wait 3 to 5 minutes, preferably 3-4 minutes, more preferably 2.5 to 4 minutes. This is followed with rinsing with water (i.e., distilled water, preferably deionized distilled water), and recalibrating. To store the pH probe after decontamination, rinse the probe with water (i.e., distilled water, preferably deionized distilled water), shake off excess, and either place the protective cap on the probe tip or add one to 10 drops of HI 70300 Storage Solution (Hanna Instruments) in the protective cap before placing on the probe tip.

The pH probe or the pH strips may be used to measure the pH at the outer labia majora, the inner labia majora, the labia minora, and the hymenal ring. For measurements at the labia and the hymenal ring the pH probe is preferred, whereas the pH strip is preferred in the vagina. For measurements at the labia, the probe or strip may be placed at the midpoint (between posterior and anterior) of the anatomic site. For measurements at the hymenal area, the pH probe is nearly perpendicular to or can vary from 45° to 135° to the anatomic site.

Measuring the Sensitivity of the Introitus with a Soft Brush and Biochemical Analyses The method may further include a method for measuring the sensitivity of the introitus using a soft tool, such as, for example, a brush. Examples of brushes includes round brushes such as, for example MasterAmp Buccal Brushes from Epicentre Biotechnologies (Madison, Wis., USA). Brushes should be soft to the tissue as defined by bristle edge, bristle length, bristle hardness. Brushes may be placed in contact with the hymenal ring as a means of measuring sensitivity and/or as a means to collect a biological tissue sample on the brush.

The method includes contacting the brush with the hymenal ring. Contact with the hymenal ring is made for at least 1 second.

Contacting the brush with the hymenal ring may include the following steps: placing the subject in a position so that the test probe can be properly situated, exposing the hymenal ring, holding the brush handle and placing the brush in light contact with the hymenal tissue at a force of between 1 psi and 0.01 psi, such as for example, less than 1 psi, less than 0.5 psi, or less than 0.1 psi and moving the brush across the desired area of tissue for tissue collection.

Prior to contacting the brush with the hymenal ring, the subject should be placed in a position so that the test probe can be properly situated. In many cases, but without being limited, this could be a gynecological examination chair. This chair has the capacity to adjust the subject's position.

Once the subject is properly positioned, spread the labia so that the hymenal area is exposed.

The next step is to grasp the handle of the brush, insert and rest the brush (MasterAmp Buccal Brush from Epicentre Biotechnologies) anywhere along the hymenal ring, preferably at the 3 or 6 or 9 or 12 o'clock positions.

To determine sensitivity to a brush, one may hold the plastic handle end between the index finger and thumb, and with a twirling rotational motion, rotate the brush for 1 to 25 cycles on the tissue surface, preferably 2 to 15 cycles, more preferably 3 to 10 cycles. Each cycle will take less than 5 seconds, preferably less than 2 seconds.

Once the brush has come in contact with the hymenal ring, the brush should be removed and cut such that the brush falls into a collecting vial (Bio Plas microcentrifuge tubes (Bio Plas 4204) and screw caps with O-rings (Bio Plas 4215R) from VWR, (VWR International LLC, Radnor Pa., USA) #20170-710 skirted conical tubes and VWR 20170-770) and, with a screw cap the vial is closed.

The vial may then be placed in dry ice and can be stored in a −70° C. (or lower) freezer for up to six months.

One or more brush samples may be collected, such as, for example, one may repeat the process between 2-10 times, preferably 2 to 5 times.

The brush samples can be extracted to measure protein, DNA, glycogen, histamine, cytokine, and metabolites.

The method may further includes having the consumer fill out a questionnaire related the experience. The questionnaire may include questions related to vaginal dryness. The questionnaire may confirm whether the consumer felt the brush and whether the contact was unpleasant. The questionnaire may ask the consumer to describe the sensation. The questionnaire may further ask questions about topics such as, for example, genital skin dryness, vaginal dryness, genital skin itch, vaginal itch, difficulty having intercourse, and combinations thereof. The questionnaire may ask the consumer to rate aspects of the contact with the brush, such as, for example, a level of unpleasantness. Ratings may be based on a scale of 1 to 10, where one represents experiencing no sensation and 10 represents the most sensation.

As stated above, brushes can be analyzed to measure protein, DNA, glycogen, histamine, cytokine, and metabolites. Brushes may be analyzed for glycogen content using the EnzyChrom™ Glycogen Assay Kit (BioAssay Systems, Hayward, Calif., USA). The EnzyChrom™ Glycogen Assay Kit utilizes a single working reagent that combines the enzymatic breakdown (hydrolysis) of glycogen via α-Amylase and Amyloglucosidase with the oxidation of glucose by glucose oxidase and detection of hydrogen peroxide via a colorimetric/fluorogenic dye reagent (from Material Safety Data Sheet accompanying the EnzyChrom™ Glycogen Assay Kit). The color intensity of the reaction product at a wavelength of 570 nm, or fluorescence intensity at $\lambda_{ex/em}=530/585$ nm is directly proportional to the glycogen concentration in the sample (Zhou M et al. Analytical Biochem 253:162-168, 1997). Glucose concentrations in the samples are determined by adding sample blank reagent containing glucose oxidase and dye without hydrolysis enzymes. Glycogen content is determined by subtracting free glucose from total glucose (glycogen+free glucose). A calibration curve is generated using a stock solution to prepare increasing concentrations of glycogen, expressed in micrograms per milliliter (μg/mL). Three Quality Control samples (high QC, medium QC and low QC) prepared from the stock solution is used to monitor assay performance during sample analysis.

Collecting a Biopsy

The array of methods may also include taking a biopsy from the labia majora, labia minora, or the introitus. The biopsy can be used for histological analysis, biochemical analysis, or transcriptomic analysis. To collect the biopsy, the skin surface is first cleansed with Betadine and then anesthetized with a topical anesthetic such as, for example, lidocaine from approximately 0.05 to 4 ml/cm². The anesthetic should be located just under the area to be biopsied. Once the anesthetic has numbed the area, the surface is cleansed with alcohol. Skin biopsies may be collected by a trained physician using a Tischler Morgan biopsy instrument (available from Gynex Corporation, Redmond, Wash., USA)

using standard aseptic techniques followed by suture closure, if necessary. If necessary, additional measures may be used for hemostasis. A Chromic suture may be used in this procedure and is expected to naturally absorb such that the removal of the suture will not be necessary. The biopsy area can be treated with Polysporin and covered with a medical gauze pad or wound bandage. A post-surgical visit may be scheduled for every subject to note healing of the biopsied site.

It is understood that more than one biopsy may be taken. The biopsy samples may be processed according to the following procedure. The biopsy samples may be used for histological evaluation by first transferring the biopsy into a pre-labeled formalin containing jar (10% neutral buffered formalin, VWR 89370-094 or equivalent). The sample may be kept in formalin overnight and then transferred into a plastic cassette containing 70% ethanol for eventual paraffin embedding, sectioning, and staining (for example, but not limited to hemotoxylin/eosin). The biopsy may also be frozen for eventual frozen sectioning and staining.

Biopsy samples may be used for transcriptomic analysis by first transferring the biopsy into a solution of RNALater (Life Technologies Cat#AM7021, Thermo Fisher Scientific, Waltham, Mass., USA) followed by an immersion in phosphate buffered saline (Life Technologies Cat. #10010031 or equivalent) and then wicked dry with a Kimwipe® (produced by Kimberly Clark Corporation, Irving, Tex., USA). The sample may then be transferred into a 1.5 ml Eppendorf tube (VWR Cat#022363204) and cap closed and placed into dry ice-ethanol bath or into a −70C (or colder) freezer until RNA processing.

Biopsy samples may be used for histological evaluation and transcriptomic analysis.

Histological evaluation may be done by the following procedure:
1. After the formalin and ethanol treatments the tissue may be cleared with xylene (VWR Cat# MK866802 or equivalent) and then embedded in paraffin in a base mold and allowed to solidify.

After the tissue block has been cooled on the cold plate and removed from the base mold, it is placed in freezer (about −4C) until sectioned.

Remove the tissue from the freezer and keep cold in an ice tray (or equivalent) on ice. Trim the block and cut to 3-4µ thickness sections using a microtome (Leica RM2125 RTS, Leica Microsystems GmbH, Wetzlar, Germany or equivalent). The sections may be placed on a water bath and any folds or wrinkles removed.

The sections can be placed on a positively charged microscope slide (VWR Cat#89500-498 or equivalent) and excess water allowed to drain or be wicked from the slides.

The slides are loaded into a Ventana Symphony Staining tray and stained for Hemotoxylin and Eosin (H&E), or other desirable histochemical stains (such as PAS, Trichrome, and others) or immunological stains (such as Ki67, CD3, S100, and others) using the Ventana Symphony system (Ventana Medical Systems, Inc., Tucson, Ariz., USA).

Biopsy samples, brush samples, or tape strip samples can be extracted to measure protein, DNA, glycogen, histamine, and metabolites.

Measurement of Glycogen

Brushes can be analyzed for glycogen content using the EnzyChrom™ Glycogen Assay Kit (BioAssay Systems, Hayward, Calif., USA). The EnzyChrom™ Glycogen Assay Kit utilizes a single working reagent that combines the enzymatic breakdown (hydrolysis) of glycogen via α-Amylase and Amyloglucosidase with the oxidation of glucose by glucose oxidase and detection of hydrogen peroxide via a colorimetric/fluorogenic dye reagent (from Material Safety Data Sheet accompanying the EnzyChrom™ Glycogen Assay Kit). The color intensity of the reaction product at a wavelength of 570 nm, or fluorescence intensity at $\lambda_{ex/em}$=530/585 nm is directly proportional to the glycogen concentration in the sample (Zhou, M. et al. Analytical Biochem 253:162-168, 1997). Glucose concentrations in the samples are determined by adding sample blank reagent containing glucose oxidase and dye without hydrolysis enzymes. Glycogen content is determined by subtracting free glucose from total glucose (glycogen+free glucose). A calibration curve is generated using a stock solution to prepare increasing concentrations of glycogen, expressed in micrograms per milliliter (µg/mL). Three Quality Control samples (high QC, medium QC and low QC) prepared from the stock solution is used to monitor assay performance during sample analysis.

The following Reagents may be used in the analysis of Glycogen:
1) EnzyChrom™ Glycogen Assay Kit, BioAssay Systems, Catalog #E2-GN-100. Store kit frozen at −20° C. for up to 6 months. The kit contains the following reagents:
   a) Assay Buffer, 12 mL
   b) Dye Reagent, 120 µL
   c) Enzyme A (α-Amylase, Amyloglucosidase), Dried
   d) Enzyme B (Glucose Oxidase), 120 µL
   e) Starch Standard, 50 mg/mL, 50 µL;
2) Water, purified by Millipore Milli-Q filtration system (Merck Millipore, Billerica, Mass., USA); or equivalent;
3) 5M Sodium chloride (NaCl), Sigma-Aldrich catalog #S5150, Sigma-Aldrich Corp., St. Louis, Mo., USA; or equivalent;
4) Protease Inhibitor Cocktail tablets, COMPLETE™, Roche Diagnostics GmbH, Mannheim, Germany, catalog #11-697-498-001;
5) Phosphate Buffered Saline (PBS) buffer packs, Sigma-Aldrich Corp., Catalog #P3813. Dilute 1 PBS buffer pack in 1 Liter of Water. Store PBS solution at room temperature for up to 1 month; or
6) Extraction Buffer ('EB', PBS+0.25M NaCl+Protease Inhibitors). Add 50 mL 5M NaCl (reagent #3) to 950 mL PBS to prepare 0.25M NaCl. Filter reagent using 0.2 µm filter flask (vacuum filter unit, sterile, Nalgene catalog 567-0020 or equivalent, Nalge Nunc International Corporation, Rochester, N.Y., USA). To this solution, dissolve 20 Protease Inhibitor tablets (reagent #4) per 1000 mL. Store at room temperature for up to 1 month.

Preparation of Brush Samples to Measure Glycogen

The following steps may be used to prepare samples to measure Glycogen.
1. Remove polypropylene tubes containing brush samples from −70° C. freezer.
2. Add Extraction Buffer (EB, Reagent #6) to each polypropylene tube:
   a) Aliquot 1.5 mL EB to each tube.
   b) Replace each screw cap, tighten caps securely.
3. Sonicate vials in ice bath (4-10° C.) for approximately 30 minutes (Ultrasonic Cleaner, Branson Ultrasonics Corporation, Danbury, Conn., USA; or equivalent).
4. Vortex tubes for 10 seconds using multi-tube vortexer (Multi-Tube Vortexer, VWR catalog # VX2500; or equivalent).
5. Using tweezers that had been cleaned with germicidal wipes (Sani-Cloth® Plus, PDI, Inc., Catalog#Q89072; or equivalent), grab and remove brush samples from each tube, while pressing the brush against inside of tube to void any residual fluid. Wipe tweezers with germicidal disposable cloths, and air dry prior to handling next brush sample.
6. Centrifuge extract for 5 minutes at 3000 rpm (room temperature; Allegra X-12R, Beckman-Coulter, Fullerton, Calif., USA; or equivalent).
7. Transfer extracts to Deep Well Plates:
   a) Uncap each tube of extract.
   b) Place tubes in liquid handler tube rack (of automated liquid handler) in order according to plate template.
   c) Using the automated liquid handler (JANUS, Perkin-Elmer, Packard MultiPROBE; or equivalent), transfer an aliquot of the supernatant (after the centrifuge step, the aliquot should approximate what is needed for an adequate measure of glycogen, an example can be 250 µL aliquot) into an empty 96-well 2 ml deep well plate (Axygen Scientific, Catalog #P-DW-20-C; or equivalent, Corning Inc., Corning N.Y., USA) for glycogen. Pending outcome, i.e., too high concentration of glycogen, it may be necessary to dilute the supernatant sample.
   d) Fasten cap mats securely on deep well plates (Titer Plate shaker, Lab-line Instruments, Inc., VWR catalog #57019-0600 or equivalent).
   e) Vortex deep well plates for 10 seconds using multi-tube vortexer.
   f) Freeze deep well plates and tubes containing extracts at −70° C. or below for future analyses.
8. If performing a second extraction, place extracted brushes into other polypropylene tubes, and repeat Steps 2-7.

Glycogen Assay
1) Equilibrate assay reagents and study sample extracts to room temperature (20-25° C.) on bench. **During experiment, keep thawed enzymes from EnzyChrom™ Assay Kit on ice or refrigerated (2-8° C.).
2) Reconstitute Enzyme A.
   a. Add 120 µL Assay Buffer to vial of dried Enzyme A
   b. Vortex vial to dissolve completely.
3) Prepare Working Standards. Dilute 50 mg/mL Starch Standard in Extraction Buffer (EB) as follows to prepare working standards. Vortex after each dilution to mix solution.
   Std1=200 µg/ml Glycogen=10 µL, Starch Standard (50 mg/mL)+2.49 mL EB
   Std2=150 µg/ml Glycogen=300 µL of 200 µg/ml Glycogen+100 µL EB
   Std3=100 µg/ml Glycogen=200 µL of 200 µg/ml Glycogen+200 µL EB
   Std4=50 µg/ml Glycogen=200 µL of 100 µg/ml Glycogen+200 µL EB
   Std5=25 µg/ml Glycogen=200 µL of 50 µg/ml Glycogen+200 µL EB
   Std6=12.5 µg/ml Glycogen=200 µL of 25 µg/ml Glycogen+200 µL EB
   Std7=6.25 µg/ml Glycogen=200 µL of 12.5 µg/ml Glycogen+200 µL EB
   Std8=3.125 µg/ml Glycogen=200 µL of 6.25 µg/ml Glycogen+200 µL EB
   Blank=EB
4) Prepare Glycogen Assay QC's
   HQC=80 µg/ml Glycogen=80 µL of 200 µg/ml Glycogen+120 µL EB
   MQC=40 µg/ml Glycogen=40 µL of 200 µg/ml Glycogen+160 µL EB
   LQC=10 µg/ml Glycogen=50 µL of MQC+150 µL EB
5) Vortex Deep well plate of sample extracts using multi-tube vortexer (30 sec, speed #7)
6) Add 10 µL Standard, Assay QC or Study samples in duplicate to each well of assay plate (clear polystyrene 96-well flat bottom plate; Becton Dickinson catalog #3072, (Becton Dickinson and Company, Franklin Lakes, N.J., USA) or equivalent) using single-channel 10 µL pipette according to 96-well plate template.
7) Prepare Working Reagent (sufficient for 64 wells) by adding 70 µL Enzyme A+70 µL Enzyme B+70 µL Dye Reagent to 6.3 mL Assay Buffer
8) Prepare Sample Blank Reagent (sufficient for 32 wells) by adding 40 µL Enzyme B+40 µL Dye Reagent to 3.6 mL Assay Buffer
9) Add 90 µL Working Reagent to each standard, assay QC and sample well of assay plate using electronic multi-channel pipettor in multi-dispense mode (2×90 µL)
10) Add 90 µL Sample Blank Reagent to each Sample Blank Well (No Enzyme A), as indicated in red on assay plate template, using electronic multi-channel pipettor in multi-dispense mode (2×90 µL).
11) Mix assay plate on titer plate shaker set at speed 5 for 10 seconds.
12) Cover plate with plastic lid; incubate on bench for 30 min. at room temperature (20-25° C.)
13) Measure the Optical Density: Read the plate at a wavelength of 570 nm with a computer-controlled microplate reader (SpectraMax 340PC$^{384}$, Molecular Devices Corporation, Sunnyvale, Calif., USA; or equivalent). The data are generated using corresponding plate reader software (SOFTmax® PRO Software for Microplate Readers, SOFTmax® PRO for Windows, Molecular Devices Corporation, Sunnyvale, Calif., USA; or equivalent). The following plate reader settings are recommended:

Instrument Parameters:
Mode: Endpt L1
Wavelength: L1: 570 nm
Auto Mix: ON

Data Analysis
Statistical Calculations:
Standards and quality controls are assayed in duplicate wells, resulting in duplicate optical density values (OD). The OD results are reported as the Mean (average) of duplicate OD values. The regression algorithm for the data analysis is a quadratic fit of the nominal concentration of the calibration standards and the mean OD values.

% CV (Coefficient of Variation)=(Standard Deviation/Mean OD)*100%

% Bias (Applicable to standards and QC's only)=((Calculated Concentration−Nominal Concentration)/Nominal Concentration)*100%

Glycogen Determination:
If there is a possibility that the samples contain glucose, separate sample blank wells should be prepared which contain no Enzyme A reagent. To calculate the glycogen concentration in each sample, subtract the glucose concentration determined in each sample blank well (No Enzyme A) from the total concentration of glycogen+glucose determined in the corresponding sample well (Enzyme A+Enzyme B):

$$[\text{Glycogen}]_{sample} = [\text{Glycogen+Glucose}]_{sample} - [\text{Glucose}]_{sample}$$

Measurement of Protein
The measurement of protein may be done using the following reagents:

1) Pierce BCA™ Protein Assay Reagent A, Thermo Scientific, Catalog #23223, 1000 mL containing sodium carbonate, sodium bicarbonate, bicinchoninic acid and sodium tartrate in 0.1 M sodium hydroxide.
2) Pierce BCA™ Protein Assay Reagent B, Thermo Scientific, Catalog #23224, 25 mL containing 4% cupric sulfate.
3) Albumin Standard, 2 mg/mL, Thermo Scientific, Catalog #23210, 50 mL, containing bovine serum albumin (BSA) at 2.0 mg/mL in 0.9% saline and 0.05% sodium azide.
4) Water, purified by Millipore Milli-Q filtration system; or equivalent.
5) 5M Sodium chloride (NaCl), Sigma catalog #S5150; or equivalent.
6) Protease Inhibitor Cocktail tablets, COMPLETE™, Roche Diagnostics GmbH, Mannheim, Germany, catalog #11-697-498-001.
7) Phosphate Buffered Saline (PBS) buffer packs, Sigma, Catalog #P3813. Dilute 1 PBS buffer pack in 1 Liter of Water. Store PBS solution at room temperature for up to 1 month.
8) Bovine Serum Albumin (BSA), 30% Sigma, Catalog #A8577; or equivalent.
9) Extraction Buffer ('EB', PBS+0.25M NaCl+Protease Inhibitors). Prepare PBS solution (reagent #5). Add 50 mL 5M NaCl (reagent #3) to 950 mL PBS to prepare 0.25M NaCl. Filter using 0.2 μm filter flask. To this solution, dissolve 20 Protease Inhibitor tablets (reagent #4) per 1000 mL. Store at room temperature for up to 1 month.

Procedure

Repeat steps 1 to 6 above from "Preparation of Brush Samples to Measure Glycogen" After step 6 of the "Preparation of Brush Samples to measure Glycogen", transfer extracts to Deep Well Plates:
1. Uncap each tube of extract.
2. Place tubes in MultiPROBE rack in order according to plate template.
3. Using the automated liquid handler, transfer an aliquot of the supernatant (after the centrifuge step, the aliquot should approximate what is needed for an adequate measure of protein, an example can be 250 μL aliquot) into an empty 96-well 2 ml deep well plate. Pending outcome, i.e., too high concentration of protein, it may be necessary to dilute the supernatant sample.
4. Fasten cap mats securely on deep well plates.
5. Vortex deep well plates for 10 seconds using multi-tube vortexer.
6. Freeze deep well plates at −70° C. or below for future analyses.

Assay

1) Prepare Bovine Serum Albumin (BSA) standards
   a) Prepare a 1 mg/mL Stock BSA solution by adding 12 mL of 2 mg/mL albumin standard (Reagent #3) to 12 mL Extraction Buffer (EB, Reagent#9).
   b) Prepare a 400 μg/mL Intermediate Stock BSA solution as follows:
      InterStock, 400 μg/mL=16 mL 1 mg/mL BSA+24 mL EB.
      Aliquot 1 mL volumes into pre-labeled tubes and freeze at −80° C. until day of analysis.
   c) To prepare BSA standards, perform 2-fold serial dilutions of InterStock (400 μg/mL). Vortex well after each dilution. The remaining volume of 500 μL of each standard is sufficient to run 4 plates in duplicate wells.
      Std1, 200 μg/mL=500 μL 400 μg/mL+500 μL EB
      Std2, 100 μg/mL=500 μL 200 μg/mL+500 μL EB
      Std3, 50 μg/mL=500 μL 100 μg/mL+500 μL EB
      Std4, 25 μg/mL=500 μL 50 μg/mL+500 μL EB
      Std5, 12.5 μg/mL=500 μL 25 μg/mL+500 μL EB
      Std6, 6.25 μg/mL=500 μL 12.5 μg/mL+500 μL EB
      Std7, 3.125 μg/mL=500 μL 6.25 μg/mL+500 μL EB
      Std8, 1.56 μg/mL=500 μL 3.125 μg/mL+500 μL EB
      Blank=500 μL EB
      *Note: Std 8 is used as an anchor point for the calibration curve and will not be considered as a calibrator. The LLOQ of the method is 3.125 μg/mL.
2) Prepare Bovine Serum Albumin (BSA) Assay QC's
   a) Prepare HQC, MQC and LQC solutions as follows:
      HQC, 75 μg/mL=3 mL 1 mg/mL BSA+37 mL EB
      MQC, 40 μg/mL=1.6 mL 1 mg/mL BSA+38.4 mL EB
      LQC, 20 μg/mL=800 μL 1 mg/mL BSA+39.2 mL EB
   b) Aliquot 300 μL of each QC into pre-labeled tubes and store frozen at −80° C. until day of analysis.
3) Prepare BCA™ working reagent.
   a) Combine 240 μL BCA™ Reagent B with 12 mL BCA™ Reagent A per 96-well plate (clear polystyrene 96-well flat bottom plate; Becton Dickinson catalog #3072, or equivalent).
   b) Vortex well.
4) Add 50 μL per well standards and QC's in duplicate into assay plate using single channel electronic pipettor in multi-dispense mode according to plate map. Vortex each tube prior to addition.
5) Vortex deep well plate of samples for 30 sec. using multi-tube vortexer.
6) Add 50 μL per well unknown samples in singlicate from deep well plate into assay plate using 8-channel electronic pipettor in reverse pipette mode according to plate map.
7) Add 100 μL per well BCA™ working reagent (prepared in step #3) using 8-channel electronic pipettor in multi-dispense mode. Cover with plastic lid.
8) Incubate plate at 39° C. for 45 minutes on dry block heater. (Note: Actual temperature of solutions in the assay plate is approximately 37° C.)
9) Measure the Optical Density: Read the plate at a wavelength of 562 nm with a computer-controlled microplate reader. The data are generated using corresponding plate reader software. The following plate reader settings are recommended:

Instrument Parameters:
Mode: Endpt L1
Wavelength: L1: 562 nm
Auto Mix: ON

Data Analysis:

Statistical Calculations:

Standards and controls are assayed in duplicate wells, resulting in duplicate optical density values (OD). The OD results are reported as the Mean (average) of duplicate OD values. The regression algorithm for the data analysis is a quadratic fit of the nominal concentration of the calibration standards and the mean OD values.

% CV (Coefficient of Variation)=(Standard Deviation/Mean OD)*100%

% Bias (Applicable to standards and QC's only)=((Calculated Concentration−Nominal Concentration)/Nominal Concentration)*100%

Acceptance Criteria:
1) Duplicate Wells (% CV)
   The % CV between duplicate OD values must meet the following criteria:
   a) % CV must be ≤20.0% for Standards 1-6 and unknown samples (if analyzed in duplicate)

b) % CV of the LLOQ (Standard 7, 3.125 μg/mL) will be excluded from acceptance criteria; see acceptance criteria for % Bias (section 2a).
c) Any unknown samples that do not meet these criteria will be reported as "NR" and must be reanalyzed in a subsequent run.
d) % CV must be ≤20.0% for at least 50% of Assay QCs at each QC level. % CV must be ≤20.0% for at least 67% of the Assay QC's.

2) % Bias
a) Standards: A minimum of 75% of the calibrators must meet the following acceptance criteria for % Bias:
   i) Back-calculated concentrations of Standards 1-6 must be within 20% of the nominal concentration (Bias±20.0%).
   ii) The back-calculated concentration of the LLOQ (Standard 7, 3.125 μg/mL) must be within 25% of the nominal concentration (Bias±25.0%). Standard 8 (1.56 μg/mL) is used as an anchor point for the calibration curve and will not be considered as a calibrator.
b) Assay QC's: At least 50% of Assay QC values must be within 20% of the nominal concentration (Bias±20.0%) at each QC level. Back-calculated concentrations of at least 67% of the Assay QC's must be within 20% of the nominal concentration (Bias±20.0%).

3) Masking of one or more blank wells is permitted only if a documented technical error occurs during the execution of the method, and that error justifies masking the blank well(s).

4) Optical density (OD) values after plate blank correction must be ≥0.001 for each well of Standards 1-7. If OD values in any standard wells are less than 0.001, samples should be reanalyzed in a subsequent run.

Measurement of Histamine

This assay is based on (1) U.S. Pat. No. 8,420,054 (which refers to a measurement from stratified epithelia and not mucosal epithelial tissue) and (2) Kerr, K., Schwartz, J. R., Filloon, T., Fieno, A., Wehmeyer, K., Szepietowski, J. C., and Mills, K. J.; *Scalp Stratum Corneum Histamine Levels: Novel Sampling Method Reveals Association with Itch Resolution in Dandruff/Seborrhoeic Dermatitis Treatment*, Acta Derm Venereol 91:404-408, 2011).

Procedure

After step 6 of the 'Preparation of Brush Samples to measure Glycogen', transfer extracts to Deep Well Plates.
1. Uncap each tube of extract.
2. Place tubes in MultiPROBE rack in order according to plate template.
3. Using the automated liquid handler, transfer an aliquot of the supernatant (after the centrifuge step, the aliquot should approximate what is needed for an adequate measure of histamine, an example can be 100 μL aliquot) into an empty 96-well deep well plate (Axygen plate). Pending outcome, i.e., too high concentration of histamine, it may be necessary to dilute the supernatant sample.
4. Samples can be supplemented with conventional reagents, such as albumin, to help prevent loss of analytes to the walls of labware.
5. Fasten cap mats securely on deep well plates.
6. Vortex deep well plates for 10 seconds using multi-tube vortexer.
7. Freeze deep well plates at −80° C. for future analyses.

Assay
1. Histamine standards and controls can be prepared by conventional methods. Histamine will be quantitated with a histamine enzyme immunoassay (EIA) kit (Histamine EIA Kit (US Distributor, Cayman Chem Co. #589651/ Histamine EIA kit Manufacture (France), SPbio #A05890).
2. A wash buffer, derivatization reagent, Histamine ACHe tracer and Ellman's Reagent can be prepared by conventional methods.
3. Standards, controls and samples are derivatized in a deep well plate.
4. Plates are washed with buffer and standards, blanks, samples and quality controls are added to the plate and are incubated for 24 hours at 4° C.
5. Plates are then washed prior to the addition of Elman's reagent and incubation in the dark at room temperature.
6. Plates can be read via standard spectrophotometry. Data analysis is conducted by standard statistical methods and calculations.

In a further embodiment, extracts obtained from the brushes are placed into a 96 well plate. Each well is spiked with a stable isotope-labeled histamine (D.sub.4-histamine) internal standard (ISTD) and diluted with acidified water. A set of histamine standards are prepared in the 96-well polypropylene plate over an appropriate calibration range in acidified water and spiked with ISTD. The standards and the brush extracts are analyzed using gradient reversed-phase high performance liquid chromatography with tandem mass spectrometry (HPLC/MS/MS). Histamine and the ISTD are monitored by positive ion electrospray (ESI). A standard curve is constructed by plotting the signal, defined here as the peak area ratio (peak area histamine/peak area ISTD), for each standard versus the mass of histamine for the corresponding standard. The mass of histamine in the calibration standards and brush extract samples are then back-calculated using the generated regression equation. The result can be reported as the mass of histamine or the result can be standardized by dividing by the amount of protein that was also found in the brush extract.

Measurement of Cytokines

While the procedure described here details an assay for interleukin 1α (IL-1α) and interleukin 1 receptor antagonist (IL-1ra), similar assays for other interleukins, such as Il-6, Il-8, Il-10 and others (not be limited) can be performed in a similar manner.

Reagents
1. Bio-Plex Pro™ Human Cytokine IL-1α Assay, Bio-Rad Laboratories, Inc. Hercules, Calif., USA, Catalog #YF0001DVXM. Kit contains the following components, all stored at 2-8° C.:
   a) Human Cytokine 23-Plex Standard, Group II (catalog #171-D60001), lyophilized
   b) IL-1α Coupled Magnetic Beads (10×, catalog #171-B6001M), 600 μL
   c) IL-1α Detection Antibodies (10×), 320 μL
   d) Streptavidin-Phycoerythrin, 100×; LIGHT SENSITIVE, store in dark.
   e) Assay Buffer, 50 mL
   f) Wash Buffer, 130 mL (catalog #171-304500, 1.5 L)
   g) Detection Antibody Diluent, 5 mL
2. Human Cytokine 27-Plex Standard, Group I (catalog #171-D50001), lyophilized
3. Bio-Plex Pro™ Human Cytokine IL-1ra set, Bio-Rad Laboratories, Inc., Catalog 171B5002M. Store at 2-8° C.:
   a) IL-1ra Coupled Magnetic Beads (10×, catalog #171-B5002M), 600 μL
   b) IL-1ra Detection Antibodies (10×), 320 μL
4. Water, purified by Waters Milli-Q filtration system; or equivalent 5. 5M Sodium chloride (NaCl), Sigma catalog #S5150; or equivalent.
6. Protease Inhibitor Cocktail tablets, COMPLETE™, Roche Diagnostics GmbH, Mannheim, Germany, catalog #11-697-498-001.
7. Phosphate Buffered Saline (PBS) buffer packs, Sigma, Catalog #P3813. Dilute 1 PBS buffer pack in 1 Liter of Water. Store PBS solution at room temperature for up to 1 month.
8. Bovine Serum Albumin (BSA), 30% Sigma, Catalog #A8577; or equivalent.
9. Extraction Buffer ('EB', PBS+0.25M NaCl+Protease Inhibitors). Prepare PBS solution (reagent #7). Add 50 mL 5M NaCl (reagent #6) to 950 mL PBS to prepare 0.25M NaCl. Filter using 0.2 µm filter flask. To this solution, dissolve 20 Protease Inhibitor tablets (reagent #6) per 1000 mL. Store at room temperature for up to 1 month.
10. Cytokine Sample Buffer ('CSB'; PBS+0.25M NaCl+Protease Inhibitors+2% BSA). Add 2 mL of 30% BSA (reagent #8) to 28 mL Cytokine Extraction Buffer (reagent #9). Store at 2-8° C. for up to one week.
11. Bio-Rad Sheath Fluid, 20 L, catalog #171-000055, or equivalent.
12. Bio-Rad Calibration Kit, catalog #171-203060.

Apparatus and Materials:
1. Automated Liquid Handler, Packard MultiPROBE, Perkin-Elmer; Waltham, Mass., USA, or equivalent.
2. Bio-Plex Suspension Array System, Bio-Rad Laboratories, Inc.; or equivalent.
3. Bio-Plex Manager Software for Bio-Plex Workstation, Bio-Rad Laboratories, Inc.; or equivalent.
4. Bio-Plex Pro II Wash Station (for magnetic and polystyrene bead based assays), catalog #300-34377, Bio-Rad Laboratories, Inc.; or equivalent.
5. Ultrasonic Cleaner, Branson Ultrasonics Corporation, Danbury, Conn., USA; or equivalent.
6. Centrifuge, Allegra X-12R, Beckman-Coulter, Fullerton, Calif., USA; or equivalent.
7. Vortex mixer, Vortex Genie-2, VWR Scientific Products Inc., Catalog #58815-178; or equivalent.
8. Titer Plate shaker, Lab-line Instruments, Inc. (VWR catalog #57019-0600), or equivalent.
9. 96-well Black, Flat-Bottom Microplates, catalog #171-025001, Bio-Rad Laboratories, Inc.
10. 96-well V-Bottom Microplates, catalog #651261, Greiner Bio-One International AG, Kremsmünster, Austria; or equivalent.
11. Aluminum Sealing Film, catalog #PCR-AS-200, Axygen Scientific; or equivalent.
12. Adhesive Microplate Sealing Film, VWR catalog #60941-062; or equivalent.
13. Disposable Reagent Reservoirs, Vista Lab, 50 mL, VWR catalog #802026-350; or equivalent.
14. Electronic multi-channel and single-channel dispensing pipettors, manual pipettors with corresponding disposable pipet tips; or equivalent.
15. Polypropylene microcentrifuge tubes, 2.0 mL, Bio-Plas, Inc., San Rafael, Calif., catalog #4204; or equivalent.
16. Microcentrifuge tubes, 1.7 mL, Sorenson BioScience, catalog #11700; or equivalent.
17. Polypropylene conical centrifuge tubes (15 ml, catalog #352097 and 50 mL, catalog #352098), Becton Dickinson, or equivalent.
18. Nunc 96-well 2 mL Deep well plates, VWR catalog #73520-474; or equivalent.
19. Sealing Mat Deep 96 Round Well Collection Plates (2.0 mL), Catalog # AM-2ML-RD Axygen Scientific; or equivalent.
20. Vacuum Filter Units, PES Membrane, 0.2 µm pore size, Sterile, NALGENE catalog #567-0020; or equivalent.

Procedure:
After step 6 of the 'Preparation of Brush Samples to measure Glycogen', transfer extracts to Deep Well Plates:
1. Uncap each tube of extract.
2. Place tubes in MultiPROBE rack in order according to plate template.
3. Add 40 µL per well 30% BSA (reagent #8) to a 96-well deep well plate.
4. Using the automated liquid handler, transfer an aliquot of the supernatant (after the centrifuge step, the aliquot should approximate what is needed for an adequate measure of cytokine, an example can be 250 µL aliquot) into an empty 96-well deep well plate (Axygen plate). Pending outcome, i.e., too high concentration of protein, it may be necessary to dilute the supernatant sample.
5. Fasten cap mats securely on deep well plates.
6. Vortex deep well plates for 10 seconds using multi-tube vortexer.
7. Freeze deep well plates at −80° C. for future analyses.

Assay
1) Equilibrate assay reagents, matrix QC's and study samples to room temperature (20-25° C.) on bench.
2) Prepare Cytokine Sample Buffer (CSB, reagent #10) by adding 2 mL of 30% BSA (reagent #8) to 28 mL Cytokine Extraction Buffer (reagent #9)
3) Prepare Human Cytokine standards
   a) Reconstitute each vial of Human Cytokine Standards: Group I (reagent #2) and Group II (reagent #1a) with 250 µL CSB. Gently vortex each vial for 3 seconds. Allow the vials to incubate for 30 minutes on ice.
   b) To prepare working standards, perform serial dilutions of Group I/II standard cocktail. Vortex well after each dilution. For concentrations of working Std 1, refer to standard value cards for each lot
   Std 1=190 µL Group I Std Cocktail+190 µL Group II Std Cocktail+215 µL CSB
   Std 2=150 µL Std 1+450 µL CSB
   Std 3=150 µL Std 2+450 µL CSB
   Std 4=150 µL Std 3+450 µL CSB
   Std 5=150 µL Std 4+450 µL CSB
   Std 6=150 µL Std 5+450 µL CSB
   Std 7=150 µL Std 6+450 µL CSB
   Std 8=150 µL Std 7+450 µL CSB
   Std 9=150 µL Std 8+450 µL CSB
   Blank=CSB

*Standard 1 is excluded (masked) from the IL-1alpha calibration curve, and will not be considered as a calibrator for IL-1alpha. Standard 2 is the ULOQ (upper limit of quantitation) of the method for IL-1alpha.

**Standard 9 is excluded (masked) from the IL-1ra calibration curve, and will not be considered as a calibrator for IL-1ra. Standard 8 is the LLOQ (lower limit of quantitation) of the method for IL-1ra.

Human Cytokine Calibrator concentrations (pg/mL)—Example: Lot #5023535, 5015357

| Standard | Dilution factor | IL-1alpha | IL-1ra |
| --- | --- | --- | --- |
| Std 1 | 1 | 25358* | 30137 |
| Std 2 | 4 | 6339.5 | 7534 |
| Std 3 | 16 | 1585 | 1883.56 |

-continued

| Standard | Dilution factor | IL-1alpha | IL-1ra |
|---|---|---|---|
| Std 4 | 64 | 396.2 | 470.89 |
| Std 5 | 256 | 99.05 | 117.7 |
| Std 6 | 1024 | 24.76 | 29.43 |
| Std 7 | 4096 | 6.19 | 7.36 |
| Std 8 | 16384 | 1.55 | 1.84 |
| Std 9 | 65536 | 0.3875 | 0.46** |

4) Prepare Human Cytokine Assay QC's
 a) To prepare Assay QC-1 (AQC-1), add 100 µL Std 1 to 900 µL CSB, Vortex.
 b) Prepare 100-fold dilution of Std 1 by adding 100 µL AQC-1 to 900 µL CSB, Vortex.
 c) To prepare Assay QC-2, add 100 µL of solution prepared in Step 4b to 400 µL CSB, Vortex.
5) Prepare 2-fold dilution of Matrix QC's adding 200 µL each freshly thawed HQC and LQC to 200 µL of CSB, vortex.
6) Prepare 1× Antibody-Immobilized Beads, protect from light.
 a) Vortex bead vials at medium speed for 30 seconds. Pipet any trapped liquid from cap.
 b) Dilute 10× beads: 575 µL IL-1α_beads (reagent #1b)+575 µL IL-1ra beads (reagent #3a)+4.6 ml Assay Buffer (reagent #1e); Vortex.
 c) Equilibrate for 20 min at room temperature prior to use.
7) Prepare Diluted Sample Extracts
 a) Vortex deep well plate of sample extracts on Multi-tube vortexer for 30 seconds.
 b) Centrifuge deep well plate for 3000 rpm to remove debris
 c) Prepare 2-fold sample dilution by adding 50 µL sample extracts to 50 µL CSB into V-bottom Addition plate according to 96-well plate template using 8-channel pipettor (reverse pipette mode).
8) Load Addition Plate
 a) Add 100 µL Standards, Assay QC's and Diluted Matrix QC's to each well of V-bottom Addition plate according to plate template using single channel pipettor (multi-dispense mode, 2×100 µL).
 b) Seal with plastic plate sealer.
9) Prime Bio-Plex Pro II Wash Station.
 a) Fill Liquid Bottle 2 with DI Water; Prime Channel 2.
 b) Attach Liquid Bottle 1 containing sufficient Bio-Plex Wash Buffer to wash station; Prime Channel 1.
10) Add 1× Antibody-Immobilized Beads into black, flat-bottom Assay Plate
 a) Vortex diluted beads for 30 seconds at medium speed.
 b) Pour diluted beads into reagent reservoir and add 50 µL to each well of black, flat bottom plate using 8-channel pipettor (multi-dispense mode).
11) Wash assay plate twice using Bio-Plex Pro II Wash Station
 a) Allow plate to sit on magnets for 15 seconds
 b) Wash wells twice using MAG X2 program
 c) RINSE DAY with Wash buffer—Channel 1.
12) Load black, flat-bottom Assay Plate
 a) Vortex Addition plate gently on plate shaker (300 rpm) for 3 seconds
 b) Add 50 µL Standards, Assay QC's, Diluted Matrix QC's, and Diluted sample extracts to each well of black, flat-bottom Assay plate according to plate template using 8-channel pipettor (reverse pipette mode).
13) Seal Assay plate with foil plate sealer, and incubate on plate shaker for 40 minutes at room temperature (20-25° C.).
 a) Seal plate with foil adhesive plate sealer to protect from light.
 b) Slowly increase plate shaker speed up to 1100 rpm (speed 10); Shake for 30 seconds.
 c) Slowly decrease plate shaker speed down to 300 rpm (speed 3)
 d) Incubate on plate shaker for 40 minutes at room temperature (20-25° C.).
14) Prepare 1× Detection Antibodies (DAb) Should be prepared 10-15 min prior to use
 a) Vortex 10×DAb for 20 s at medium speed, followed by a 30 sec. quick spin.
 b) Add 300 µL of 10×IL-1α_DAb (reagent #1c)+300 µL of 10×IL-1ra DAb (reagent #3b)+2.4 ml Detection Antibody Diluent (reagent #1g).
15) Wash assay plate three times using Bio-Plex Pro II Wash Station
 a) Allow plate to sit on magnets for 15 seconds
 b) Wash wells twice using MAG X3 program
 c) RINSE DAY with Wash buffer—Channel 1.
16) Add 1× Detection Antibodies to black, flat-bottom Assay Plate
 a) Vortex 1× Detection Antibodies gently for 3 seconds
 b) Pour into reagent reservoir and add 25 µL 1× Detection Antibodies to each well using 8-channel pipettor (multi-dispense mode).
17) Seal Assay plate with foil plate sealer, and incubate on plate shaker for 30 minutes at room temperature (20-25° C.).
 a) Seal plate with foil adhesive plate sealer to protect from light.
 b) Slowly increase plate shaker speed up to 1100 rpm (speed 10); Shake for 30 seconds.
 c) Slowly decrease plate shaker speed down to 300 rpm (speed 3)
 d) Incubate on plate shaker for 30 minutes at room temperature (20-25° C.).
18) Prepare 1× Streptavidin-PE. Should be prepared 10 min prior to use; Protect from light.
 a) Vortex 100× Streptavidin-PE (reagent #1d) for 20 sec. at medium speed, followed by a 30 sec. quick spin
 b) Add 60 µL of 100× Streptavidin-PE in 5.94 ml Assay Buffer. Vortex well.
19) Wash assay plate three times using Bio-Plex Pro II Wash Station
 a) Allow plate to sit on magnets for 15 seconds
 b) Wash wells twice using MAG X3 program
 c) RINSE DAY with Wash buffer—Channel 1.
20) Add 1× Streptavidin-PE to black, flat-bottom Assay Plate
 a) Vortex 1× Streptavidin-PE for 5 seconds at medium speed.
 b) Pour into reagent reservoir and add 50 µL 1× Streptavidin-PE to each well using 8-channel pipettor (multi-dispense mode).
21) Seal Assay plate with foil plate sealer, and incubate on plate shaker for 10 minutes at room temperature (20-25° C.).
 a) Seal plate with foil adhesive plate sealer to protect from light.
 b) Slowly increase plate shaker speed up to 1100 rpm (speed 10); Shake for 30 seconds.
 c) Slowly decrease plate shaker speed down to 300 rpm (speed 3)
 d) Incubate on plate shaker for 10 minutes at room temperature (20-25° C.).
22) Wash assay plate three times using Bio-Plex Pro II Wash Station
 a) Allow plate to sit on magnets for 15 seconds
 b) Wash wells twice using MAG X3 program
 c) RINSE NIGHT with Water—Channel 2

23) Resuspend Beads in Assay Buffer
   a) Add 120 microL Assay Buffer to each well using 8-channel pipettor.
   b) Seal plate with foil adhesive plate sealer to protect from light.
   c) Slowly increase plate shaker speed up to 1100 rpm (speed 10); Shake for 30 seconds.
24) Run plate on Bio-Plex Suspension Array Reader. Read 50 beads per region, sample volume: 50 μL. DD gates: 5,000 to 25,000
25) If analyzing a second assay plate, repeat steps 3-25.

96-well Plate Template

|   | 1 | 2 | 3 | 4 | 5 | 6 | 7 | 8 | 9 | 10 | 11 | 12 |
|---|---|---|---|---|---|---|---|---|---|----|----|----|
| A | Std09 | Std05 | Std01 | UNK1 | UNK9 | UNK17 | UNK25 | UNK33 | UNK41 | UNK49 | UNK57 | CSB |
| B | Std09 | Std05 | Std01 | UNK2 | UNK10 | UNK18 | UNK26 | UNK34 | UNK42 | UNK50 | UNK58 | CSB |
| C | Std08 | Std04 | AQC 1-1 | UNK3 | UNK11 | UNK19 | UNK27 | UNK35 | UNK43 | UNK51 | UNK59 | HQC-2 |
| D | Std08 | Std04 | AQC 1-2 | UNK4 | UNK12 | UNK20 | UNK28 | UNK36 | UNK44 | UNK52 | UNK60 | LQC-2 |
| E | Std07 | Std03 | AQC 2-1 | UNK5 | UNK13 | UNK21 | UNK29 | UNK37 | UNK45 | UNK53 | UNK61 | AQC 1-3 |
| F | Std07 | Std03 | AQC 2-2 | UNK6 | UNK14 | UNK22 | UNK30 | UNK38 | UNK46 | UNK54 | UNK62 | AQC 1-4 |
| G | Std06 | Std02 | HQC-1 | UNK7 | UNK15 | UNK23 | UNK31 | UNK39 | UNK47 | UNK55 | UNK63 | AQC 2-3 |
| H | Std06 | Std02 | LQC-1 | UNK8 | UNK16 | UNK24 | UNK32 | UNK40 | UNK48 | UNK56 | UNK64 | AQC 2-4 |

Data Analysis:
Statistical Calculations:

Standards are assayed in duplicate wells, resulting in duplicate fluorescence intensity (FI) values. The mean (average) of duplicate H values of the standards for each cytokine are plotted and analyzed using 5-parameter logistic fit (5-PL) nonlinear regression curve-fitting method. The concentration of each cytokine is interpolated from the standard curve.

% CV (Coefficient of Variation)=(Standard Deviation/Mean FI)*100%

% Bias (Applicable to standards and assay QC's only)=((Calculated Concentration−Nominal Concentration)/Nominal Concentration)*100%

Recovery (Applicable to standards and assay QC's only)=(Calculated Concentration/Nominal Concentration)*100%

Calculated concentration=Observed concentration; interpolated from standard curve Nominal concentration=Expected concentration Acceptance Criteria:
1) Duplicate Wells (% CV)
The % CV between duplicate FI values must meet the following criteria:
   a) % CV must be $\mu\_20\%$ for at least 75% of the standards for each cytokine (or $\mu\_25\%$ for the LLOQ (lower limit of quantitation).
   b) % CV must be $\mu\_20\%$ for specimens (if run in duplicate). Any unknown specimens that do not meet these criteria will be reported as "NR" and must be reanalyzed in a subsequent run.
2) % Bias (% Recovery)

Measurement of Metabolites:

After steps 6 of 'Preparation of Brush Samples to measure Glycogen', aliquots of the supernatant were transferred into fresh tubes and frozen to at −70° C. or below for future analyses. The samples were shipped to Metabolon, Inc. (Durham, N.C.) for identification and quantification of metabolites. Heirarchal mapping of functional elements was performed including metabolites associated with (1) oxidative stress (examples not limited to glutathione, S-methyl-glutathione, cysteine, methionine), (2) protein metabolism (examples not limited to methionine, N-formylmethionine, alanylglutamate, threonylleucine), (3) glycogen breakdown (examples not limited to maltohexaose, maltopentaose, maltose, maltotriose), (4) pentose phosphate pathway or PPP (examples not limited to arabitol, sorbitol, mannitol), (5) inflammation (examples not limited to 12-hydroxyeicosatetraenoic acid or 12-HETE, arachidonate, linoleate), and membrane formation (examples not limited to choline phosphate, phosphoethanolamine, glycerophosphoethanolamine).

In addition to the hymenal area, superficial tissue samples can also be obtained from the labial areas using a tape strip collection procedure, followed with extraction, and analysis. D-Squame tapes from Cuderm can be used to collect samples.

Figure 1:
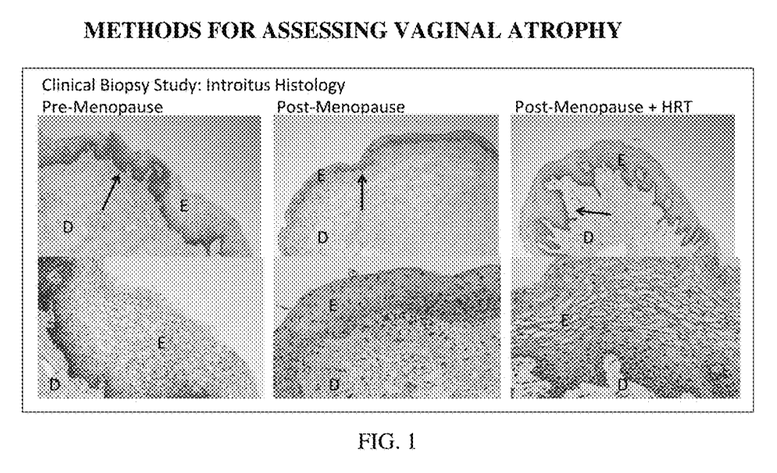
FIG. 1 shows images of biopsies taken at the introitus.
Figure 2:
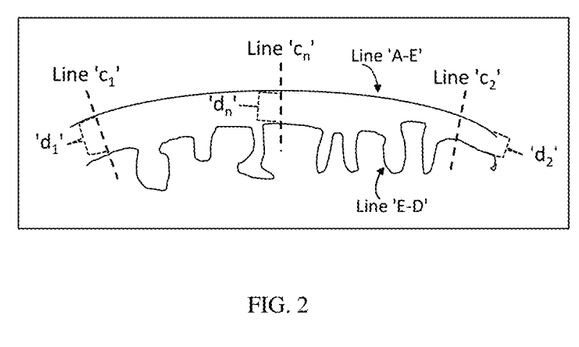
FIG. 2 shows an image used in the measurement of epithelial tissue.

Applicants have found that the mucosal tissue of the introitus undergoes considerable change similar to the vaginal canal. As shown in FIG. 1A-C, the histological images show considerable anatomic and histologic changes at the introitus that are similar to the vagina. For example, the epithelial tissue (marked by 'E') in samples taken from a menopausal group appears considerably thinner relative to the samples taken from a pre-menopausal group. The epithelial cells that are typically filled with glycogen are flat. A new feature associated with the introitus and effected by menopausal status is the appearance of rete ridges or rete pegs (noted by the arrows). These are epithelial tissue intrusions into the dermis and serve to stabilize or provide strong bonding to the underlying dermis (marked by 'D'). This feature is typically observed for air-exposed stratified squamous epithelia. With menopause, there is attenuation or shortening/disappearance of the rete pegs relative to pre-menopause. With HRT treatment both the thickness of the epithelial tissue and size of the rete pegs increases. In FIG. 2, one can measure the relative thickness of the epithelial tissue and the relative abundance of the rete pegs with the following formula (using either 4× or 10× magnified images, preferably a 10× image):

Curvilinear line 'A-E' refers to the interface between the epithelial tissue and the air or paraffin interface. Curvilinear line 'E-D' refers to the border between the epithelial tissue and dermal tissue. Create borders of the tissue image such that a perpendicular line (or nearly so line) is drawn across the A-E and E-D lines ($c_1$ and $c_2$) in areas that are devoid of rete pegs. Determine the length of lines A-E and E-D (measured in pixels) between the borders $c_1$ and $c_2$. To determine an approximation of rete peg abundance, divide the length of E-D by A-E. Create additional perpendicular lines (or nearly so lines) drawn across the A-E and E-D lines ($c_n$) and measure epithelial thickness (measured in pixels). To determine an approximation of the epithelial thickness use the following formula:

$$\frac{(\text{length } A - E) + (\text{length } E - D)}{2} \times (\text{average length of '}d\text{'})$$
$$\overline{(\text{length of } E - D)}$$

Similarly, applicants have found that the use of transcriptomic heat maps may be used to determine changes in the hymenal area and the labia majora.

Gene activity analysis (also called transcriptomics may be done on a biopsy obtained from the labia or hymenal area to determine the changes associated with menopause and treatment effects. Transcriptional profiling is known to one of ordinary skill in the art as shown by Cotreau et al. (Cotreau M M, Chennathukuzhi V M, Harris H A, Han L, Dorner A J, Apseloff G, Varadarajan U, Hatstat E, Zakaria M, Strahs A L, Crabtree J S, Winneker R C, and Jelinsky S A. Maturitas 58:366-376, 2007) wherein transcriptional profiling was derived from a vaginal biopsy to determine the effects of a dermal patch of estrogen on vaginal atrophy. A broader approach to transcriptomic analysis in which data are analyzed for hierarchical clustering to visualize global patterns can be performed using OmniViz Version 6.1.4 software (Instem Scientific, Cambridge, UK).

Biological theme analysis to identify regulated biological processes can be performed using Gene Ontology terms and methods that are similar to the DAVID Bioinformatics Resources (david.abcc.ncifcrf.gov) and can also be found in the following references, (1) Huang da, W., B. T. Sherman, and R. A. Lempicki, *Systematic and integrative analysis of large gene lists using DAVID bioinformatics resources.* Nat Protoc, 2009. 4(1): p. 44-57, and (2) Huang da, W., B. T. Sherman, and R. A. Lempicki, *Bioinformatics enrichment tools: paths toward the comprehensive functional analysis of large gene lists.* Nucleic Acids Res, 2009. 37(1): p. 1-13.

The purified RNA obtained from the extracted biopsy was converted to biotin-labeled cRNA copies using the Affymetrix HT 3' IVT Express kit (Cat. #901253, Santa Clara, Calif., USA) and protocol provided by Affymetrix as executed on a Beckman Biomek® $FX^P$ Laboratory Automation Workstation (Beckman Cat. #A31842, Beckman Coulter, Brea, Calif., USA). Biotinylated cRNA was fragmented by limited alkaline hydrolysis and then hybridized overnight to Affymetrix GeneTitan® HG-U219 array plates using the Affymetrix GeneTitan® instrument and protocol provided by Affymetrix. Following processing, chip images were converted to numeric data using the PLIER algorithm as executed in the Affymetrix GeneChip Expression Console.

Specifically the Applicants found that of the approximately 49,000 gene probe sets corresponding to approximately 22,000 genes, one would expect approximately 2500 probe sets or about 5% to be significant by chance alone at p<0.05 (t-test comparison). Applicants have discovered that estrogen status of the woman (Pre-menopause vs. Post-Menopause, or Post-menopause vs. Post-menopause+HRT) results in a significant change in gene probe expression more than by chance alone. For the samples obtained at the hymenal ring, treatment with HRT results in about 18% change of the gene probes whose activity changed (8787/49293), that is transcriptional activity increased or decreased, whereas at the labia majora approximately 8% of the gene probe sets are significantly effected by HRT. When the data are filtered at a more stringent p<0.01 (t-test comparison), hierarchal gene cluster analysis of the hymenal ring sample shows a total of 9060 gene probe sets met this criteria. Of those gene probes that increased in post-menopausal women (5610 gene probe sets), 93.7% (5256) were reversed by HRT treatment.

Of those gene probes that decreased in post-menopausal women (3450), 97.1% (3349) were reversed by HRT treatment. For the samples obtained at the labia majopra, when the data were similarly filtered with the same stringency, a total of 1620 gene probe sets met this criterion. Of those gene probes that increased in post-menopausal women (846 gene probe sets), 89.4% (756) were reversed by HRT treatment. Of those gene probes that decreased in post-menopausal women (774), 84.9% (657) were reversed by HRT treatment.

Specifically, Applicants have found that collagen related genes are regulated at the hymenal area, which is the changes (increases or decreases) associated with menopause reversed with menopause treatment. Further, senescence related genes are similarly regulated by menopausal atrophy treatments and change between pre-menopause and those experiencing vaginal atrophy. Further mitochondrial structural proteins, ribosomal RNAs, and enzymes associated with energy production including electron transport chain and cellular respiration are similarly regulated by menopausal atrophy treatments and change between pre-menopause and those experiencing vaginal atrophy. Applicants have found that changes in the gene probe set to assess atrophy may be limited to gene probes associated with collagen expression. Applicants have found that changes in the gene probe set to assess atrophy may be limited to cell cycle progression.

Applicants have found that pre-menopausal women versus post-menopausal women experiencing vaginal atrophy differ in their clinical atrophy scores and in vaginal dryness and painful intercourse grades. Applicants have also found that the pH at the hymenal area most closely correlates to the pH in the vaginal canal. Applicants have also found that the pH of the labia majora increases a measureable amount with the onset of menopause and is reversed with menopausal atrophy treatments.

Testing at the labia majora, labia minora, and/or introitus allows for the assessment of vaginal atrophy without the need to insert a speculum inside the vaginal canal. The array of methods above allow for the assessment using pH, brush sensitivity, glycogen level assessment from a brush or biopsy, protein assessment from a brush or biopsy, analysis of the epithelial cells taken from a biopsy, the use of heat maps, gene activity to determine gene expression, or combinations thereof.

Applicants have found that the methods above may be used to assess the extent of vaginal atrophy prior and post a treatment regime.

In an embodiment, the array of methods may be used to assess a treatment. The treatment may reduce the pH relative to atrophy by 0.1 to 2.0 pH units or by 0.3 units to 1.5 units.

In an embodiment, the array of methods may be used to assess a treatment. The treatment may result in the introitus having a pH of 3.5 to 5.8 units.

In an embodiment, the array of methods may be used to assess a treatment by analyzing epithelial cells at the introitus and the abundance of rete pegs in the hymenal ring. A treatment may show an effect of increasing the rete abundance by 10 to 100%.

In an embodiment, the method of analyzing epithelial cells at the introitus may further include measuring the thickness of the hymenal epithelia before and after a treatment. A treatment may show an effect of increasing the thickness relative to atrophy by 10 to 300%.

In an embodiment, the method of analyzing glycogen at the introitus may further include measuring the amount of glycogen before and after treatment. A treatment may show an effect of increasing the amount of glycogen by 10 to 300%.

In an embodiment, the method of analyzing components of protein synthesis such as N-formylmethionine and/or methionine at the introitus may further include measuring the amount of N-formylmethionine and/or methionine before and after treatment. A treatment may show an effect of increasing components of protein synthesis such as N-formylmethionine and/or methionine by 10 to 100%

In an embodiment, the method of analyzing components of glycogen metabolism such as maltohexaose, and/or maltopentaose, and/or maltotriose, and/or maltose at the introitus may further include measuring the amount of maltohexaose, and/or maltopentaose, and/or maltotriose, and/or maltose before and after treatment. A treatment may show an effect of increasing components of glycogen metabolism such as maltohexaose, and/or maltopentaose, and/or maltotriose, and/or maltose by 10 to 100%.

In an embodiment, the method of analyzing components of alcohol production such as mannitol, and/or sorbitol, and/or arabitol at the introitus may further include measuring the amount of mannitol, and/or sorbitol, and/or arabitol before and after treatment. A treatment may show an effect of decreasing components of the alcohol production such as mannitol, and/or sorbitol, and/or arabitol by 10 to 400%.

In an embodiment, the method of analyzing components of inflammation such as 12-HETE, and/or arachidonate, and/or linoleate at the introitus may further include measuring the amount of 12-HETE, and/or arachidonate, and/or linoleate before and after treatment. A treatment may show an effect of decreasing components of inflammation such as 12-HETE, and/or arachidonate, and/or linoleate by 10 to 400%.

In an embodiment, the method of analyzing gene probe activity at the introitus may further include measuring transcriptomic gene probe changes before and after treatment. A treatment may show an effect of increasing transcriptomic gene probe activity in 1 to 90% of the total gene probe set.

A treatment may show an effect of decreasing transcriptomic gene probe activity in 1 to 90% of the total gene probe set.

Treatments may include a labially or vaginally applied emollient comprised of estrogenic compounds, isoflavones or phytosteroids, and skin treatment agents (such as but not limited to niacinamide and/or panthenol), hyaluronin, fatty oils, buffered acids, moisturizers, and mixtures thereof. Treatments may further include an oral or dermal delivery system comprised of estrogen. Estrogen treatment, generally via oral or dermal administration, is also referred to as hormone replacement therapy or HRT.

In one embodiment, the oil material is selected to have an oil stability index ("OSI") of at least about 10 hours, at least about 14 hours, or at least about 18 hours at 110° C. or 120° C. A common measure for monitoring oxidative stability is the development of hydroperoxides (peroxide value or PV) over time. Oxidative stability can also be expressed in terms of the time required to obtain secondary oxidation products when aerating a sample at elevated temperature. This time, called the Oil Stability Index or OSI, is normally measured at 110C or 120C [Amer Oil Chem Soc Oil Stability Index Method Cd 12b-92] using the Rancimat instrument (Brinkmann Instruments, Inc.) or the OSI instrument (Omnion, Inc.). It is believed that oil materials comprising relatively high levels of oleic acid tend to be more stable in the context of the present invention. In one embodiment, the oil material comprises at least about 10%, from about 10% to about 80%, or from about 15% to about 70%, by weight of the oil material, of oleic acid. In one embodiment, the lotion composition comprises from about 0.0005% to about 16%, from about 0.005% to about 8%, or from about 0.01% to about 2.4%, by weight of the lotion composition, of oleic acid. Non-limiting examples of suitable oil materials exhibiting the desired properties described herein include oleic canola Oil (*Brassica campestris, B. napus, B. rapa*; characterized by having an oleic content greater than 70%, e.g., hi oleic canola oil, very high oleic canola oil, or partially hydrogenated canola oil), manila kernel oil (*Sclerocarya birrea*), palm oil (*Elaeis Guineensis* Oil), palm olein, palm stearin, palm superolein, pecan oil, pumpkin seed oil, oleic safflower oil (*Carthamus Tinctorius*; characterized by having an oleic content of greater than about 30% and omega-6 fatty acid content of less than about 50%, e.g., hi oleic safflower oil), sesame oil (*Sesamum indicum, S. oreintale*), soybean oil (*Glycine max*, e.g., hi oleic soybean, low linolenic soybean oil, partially hydrogenated), oleic sunflower oil (*Helianthus annus*; characterized by having an oleic content of greater than about 40%, e.g., mid oleic sunflower or high oleic sunflower oil), and mixtures thereof. Oleic canola oil, palm oil, sesame oil, hi oleic safflower oil, hi oleic soybean oil, mid oleic sunflower oil, and high oleic sunflower oil are common plant-bred derived oils and may be also be derived from non genetically modified organisms (non GMO). Non-limiting examples of oil materials are commercially-available from a number of vendors, including Cargill for partially hydrogenated soybean oil (i.e., Preference® 110W Soybean Oil or Preference® 300 Hi Stability Soybean Oil), mid oleic sunflower oil (i.e., NuSun® Mid-Oleic Sunflower Oil), high oleic sunflower oil (i.e., Clear Valley® High Oleic Sunflower Oil), high oleic canola oil, very high oleic canola, and partially hydrogenated low erucic rapeseed oil (i.e., Clear Valley® 65 High Oleic Canola Oil and Clear Valley® 75 High Oleic Canola Oil); Lambert Technology for high oleic canola oil (i.e., Oleocal C104); Arch Personal Care for manila kernel oil; Pioneer for high oleic soybean oil (i.e., Plenish®); Asoyia for low linolenic soybean oil (i.e., Ultra Low Linolenic Soybean Oil®); and Dipasa, Inc. for refined sesame oil.

The skin treatment agents can further comprise supplemental skin treatment agents such as niacinamide, zinc oxide, hexamidine, panthenol, and the like, and mixtures thereof. Suitable skin treatment agents are described in US 2003/0082219 A1.

In one embodiment, the moisturizer typically present in quantities of 0.1-20% (w/w), preferably of 1-15% (w/w), and more preferably 2-12% (w/w). Suitable moisturizers are e g, amino acids, pyrrolidone carboxylic acid, lactic acid and its salts, lactitol, urea and urea derivatives, ureic acid, glucosamine, creatinine, crack products of collagen, chitosan or chitosan salts/-derivatives, and in particular polyols and polyol derivatives (e. g. ethylene glycol, propylene glycol, butylene glycol, pentylene glycol, hexylene glycol, erythrite, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20, PEG-135, PEG 150), sugar and sugar derivatives (e.g., fructose, glucose, maltose, maltitol, mannite, inosite, sorbite, sorbitylsilandiol, sucrose, trehalose, xylose, xylit, glucuronic acid and its salts), ethoxylated sorbit (Sorbeth-6, Sorbeth-20, Sorbeth-30, Sorbeth-40), honey and hydrogenated honey, hydrogenated starch hydrolysates, as well as mixtures of hydrogenated wheat protein, hydrolyzed milk protein, lecithin, pythantriol, hyaluronic acid and salts thereof, and PEG-20-acetatecopolymers. Particularly preferred moisturizers are glycerine, diglycerine and triglycerine.

In one embodiment, the estrogenic material is typically present in quantities of 0.001-10%, preferably 0.01-8%, and more preferably 0.05-5%. Suitable estrogenic materials are estradiol, estrone, and estriol.

Phytosteroids represent materials that are extracted from plants. Representative ingredients can include steroidal and non-steroidal structures both possessing steroid-like biological activity. Examples of steroidal materials include vegetable oil derived steroids, i.e., sitosterol, stigmasterol, and campesterol. Non-steroidal structures include isoflavones, flavones, and coumestans. Isoflavones, which include genestein, daidzein, formononetin, and equol have been identified as useful treatments for symptoms associated with menopause and perimenopause (U.S. Pat. No. 5,498,631 to GORBACH Mar. 12, 1996), depression and dementia (U.S. Pat. No. 5,733,926 to GORBACH Mar. 31, 1998, U.S. Pat. No. 6,083,526 to GORBACH, Jul. 4, 2000), skin wrinkling (U.S. Pat. No. 6,060,070 to GORBACH May 9, 2000), and cancer (WO 2004022023 to NOVOGEN).

In one embodiment, the isoflavone material is typically present in quantities of 0.001% to about 40% of isoflavones, preferably 0.001% to about 4%, more preferably 0.01% to about 2% isoflavones. The isoflavones can be selected from the group consisting of soy isoflavones, clover isoflavones, genestein, daidzein, formononetin, biochanin A, S-equol, R-equol or a mimetic plant extract. By mimetic plant extract is meant, in the context of the application, any plant extract capable of mimicking the action of the isoflavones identified.

In an embodiment, one or more of the methods within the array of methods may be included in a kit for assessing the efficacy of a vaginal atrophy treatment regimen that comprises a pretreatment assessment method; a topical treatment for application to the labia majora, labia minora, introitus, vagina, or combinations thereof; a post treatment assessment method for vaginal atrophy; and a means to determine the difference between the pretreatment and post-treatment assessments of vaginal atrophy to assess the overall effect of the topical treatment. The pretreatment assessment method and post treatment assessment method may be one or more of any of the above described methods for assessing vaginal atrophy, including but not limited to: measuring pH at the labia majora, labia minora, introitus, or combinations thereof; determining brush sensitivity at the introitus; assessing glycogen at the introitus; a biopsy analysis of the epithelial cells at the introitus; assessing protein testing at the introitus; transcriptnomics heat mapping at the labia major or the labia minora; or evaluating gene expression to the labia majora, labia minora, introitus, vagina, or combinations thereof.

The kit may further include one or more one or more absorbent articles used in combination with the assessment method. As used herein, absorbent article may include a feminine hygiene article, a feminine hygiene pad, an interlabial, a feminine hygiene liner, an adult incontinent pad, an adult incontinent pant, an adult incontinent diaper, a sterile gauze, a wet wipe, and a wound dressing.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for identifying urogenital changes associated with vaginal atrophy, the method comprising:
   a. measuring pH at the labia majora, labia minora, introitus, or combinations thereof;
   b. determining brush sensitivity at the introitus;
   c. assessing glycogen amount at the introitus;
   d. analyzing epithelial cells sampled at the introitus;
   e. assessing protein amount at the introitus or the labia majora or the labia minora;
   f. assessing metabolites amounts at the introitus or the labia majora or the labia minora;
   g. assessing histamine amount at the introitus or the labia majora or the labia minora;
   h. transcriptomic heat mapping at the labia majora or the labia minora or the introitus; and
   i. evaluating gene expression at the labia majora using a gene probe set.

2. The method of claim 1, wherein the method of measuring pH further comprises using a pH probe.

3. The method of claim 1, wherein the changes in gene expression determined by the gene probe set are limited to gene expressions associated with collagen expression.

4. The method of claim 1, wherein the changes in gene expression determined by the gene probe set are limited to cell cycle progression.

5. The method of claim 1, wherein the method is used to assess the extent of vaginal atrophy prior and post a treatment regime.

6. The method of claim 5, wherein the treatment shows an effect of reducing the pH relative to atrophy by 0.1 to 2.0 pH units.

7. The method of claim 5, wherein the treatment shows an effect of reducing pH relative to atrophy by 0.3 units to 1.5 units.

8. The method of claim 5, wherein the treatment results in the introitus having a pH of 3.5 to 5.8 units.

9. The method of claim 5, wherein the treatment is a urogenitally or vaginally applied emollient comprised of estrogen, isoflavones, niacinamide, hyaluronin, panthenol, fatty oils, buffered acids, and mixtures thereof.

10. The method of claim 5, wherein the treatment is an oral or dermal delivery system comprised of estrogen.

11. The method of claim 1, wherein analyzing epithelial cells at the introitus further comprises measuring the abundance of rete pegs in the hymenal ring, wherein the method further comprises a treatment, and wherein the treatment shows an effect of increasing the rete abundance by 10 to 100%.

12. The method of claim 1, wherein analyzing epithelial cells at the introitus further comprises measuring the thickness of the hymenal epithelia, wherein the method further comprises a treatment, and wherein the treatment shows an effect of increasing the thickness relative to atrophy by 10 to 300%.

* * * * *